(12) United States Patent
Jiang et al.

(10) Patent No.: US 11,913,863 B2
(45) Date of Patent: Feb. 27, 2024

(54) MICROPLASTIC DETECTION DEVICE AND METHOD BASED ON PYROLYSIS-MASS SPECTROMETRY TECHNOLOGY

(71) Applicant: HARBIN INSTITUTE OF TECHNOLOGY, WEIHAI, Weihai (CN)

(72) Inventors: Jie Jiang, Weihai (CN); Xiangnan Zhang, Weihai (CN); Na Li, Weihai (CN); Hengnan Zhang, Weihai (CN); Jing Gao, Weihai (CN)

(73) Assignee: HARBIN INSTITUTE OF TECHNOLOGY, WEIHAI, Weihai (CN)

( * ) Notice: Subject to any disclaimer, the term of this patent is extended or adjusted under 35 U.S.C. 154(b) by 458 days.

(21) Appl. No.: 17/384,811

(22) Filed: Jul. 26, 2021

(65) Prior Publication Data

US 2021/0348994 A1  Nov. 11, 2021

Related U.S. Application Data

(63) Continuation of application No. PCT/CN2020/072954, filed on Jan. 19, 2020.

(30) Foreign Application Priority Data

Jan. 28, 2019 (CN) .......................... 201910080903.8

(51) Int. Cl.
*G01N 1/44* (2006.01)
*G01N 27/62* (2021.01)
(Continued)

(52) U.S. Cl.
CPC ............. *G01N 1/44* (2013.01); *G01N 27/623* (2021.01); *G01N 27/626* (2013.01); *G01N 33/442* (2013.01)

(58) Field of Classification Search
CPC ...... G01N 33/442; G01N 1/44; G01N 27/623; G01N 27/626

See application file for complete search history.

(56) References Cited

U.S. PATENT DOCUMENTS 4,159,894 A * 7/1979 Hu ......................... G01N 30/12
422/89
5,002,894 A * 3/1991 Shakkottai ............. G01N 33/46
422/89

(Continued)

FOREIGN PATENT DOCUMENTS

CN 201041538 Y 3/2008
CN 206177876 U 5/2017

OTHER PUBLICATIONS

Microplastic Abundance and Composition in Western Lake Superior As Determined via Microscopy, Pyr-GC/MS, and FTIR Erik Hendrickson,† Elizabeth C. Minor,*,‡ and Kathryn Schreiner Environ. Sci. Technol. 2018, 52, 1787-1796 (Year: 2018).*

(Continued)

*Primary Examiner* — Sean M Luck

(57) ABSTRACT

The present invention relates to a microplastic detection device and method based on a pyrolysis-mass spectrometry technology. The microplastic detection device based on a pyrolysis-mass spectrometry technology provided by the present invention is substantially a sealed gas path device system formed connected via pipelines. The device includes a working gas source, a pyrolysis device, a filter and a mass spectrometer which are connected in sequence. After a microplastic sample is placed into the pyrolysis device, the microplastic sample is decomposed in the pyrolysis device, and pyrolysis products from the microplastic sample driven by a carrier gas of the working gas source enter the mass spectrometer for detection and analysis after being filtered by the filter. Furthermore, the present invention provides a (Continued)

microplastic detection method based on a pyrolysis-mass spectrometry. The present invention is widely applied to the field of a microplastic detection technology.

10 Claims, 1 Drawing Sheet

(51) Int. Cl.
 *G01N 33/44* (2006.01)
 *G01N 27/626* (2021.01)
 *G01N 27/623* (2021.01)

(56) References Cited

U.S. PATENT DOCUMENTS

| | | | |
|---|---|---|---|
| 2001/0014478 A1* | 8/2001 | Schaedlich | G01N 33/0045 73/23.31 |
| 2008/0053192 A1* | 3/2008 | Parekh | G01N 30/20 422/80 |
| 2011/0100211 A1* | 5/2011 | Kiyono | B01D 53/22 95/45 |
| 2011/0262336 A1* | 10/2011 | Rauleder | C01B 32/05 422/600 |
| 2013/0152793 A1* | 6/2013 | Bhuwania | B01D 69/08 423/447.4 |
| 2016/0097748 A1* | 4/2016 | Hansen | G01N 30/16 73/23.37 |
| 2017/0165612 A1* | 6/2017 | Dastgheib | B01D 71/021 |

OTHER PUBLICATIONS

International Search Report issued in corresponding International application No. PCT/CN2020/072954, dated Apr. 10, 2020.
International Searching Authority for No. PCT/CN2020/072954, dated Apr. 10, 2020.
Marine Pollution Bulletin, journal, available online Oct. 11, 2018, (5 pages).

* cited by examiner

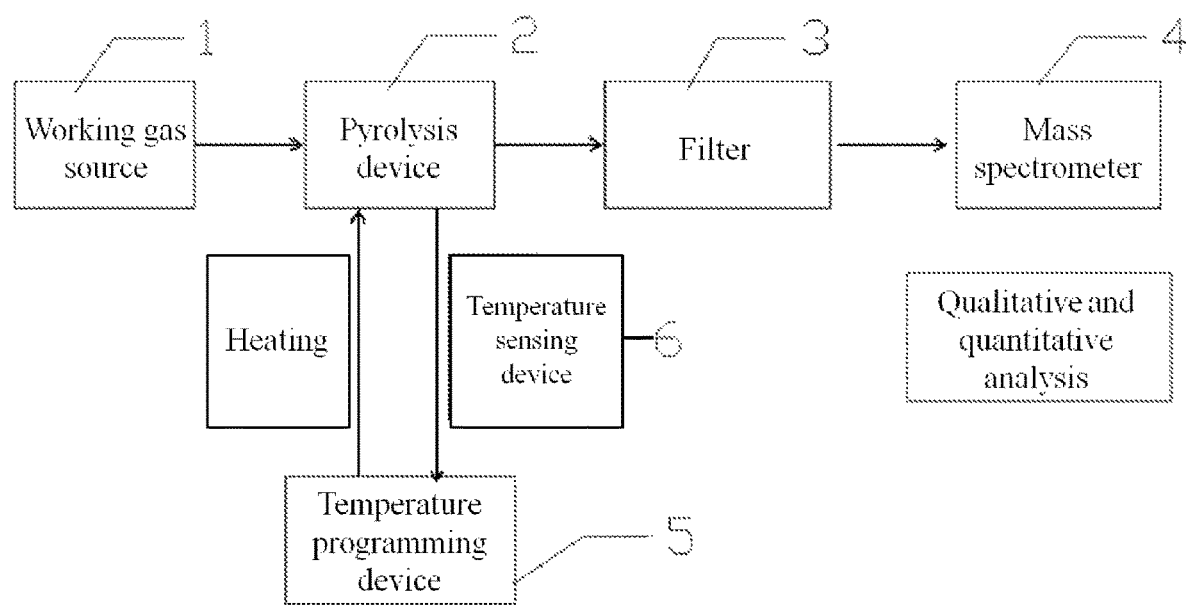

MICROPLASTIC DETECTION DEVICE AND METHOD BASED ON PYROLYSIS-MASS SPECTROMETRY TECHNOLOGY

CROSS REFERENCE OF RELATED APPLICATIONS

The present application is a continuation-application of international (PCT) patent Application No. PCT/CN2020/072954 filed on Jan. 19, 2020, which claims priority of Chinese patent Application No. 201910080903.8 filed on Jan. 28, 2019. The entire contents of the above applications are hereby incorporated by reference.

TECHNICAL FIELD

The present invention relates to the field of microplastics detection technology, and more particularly to a microplastic detection apparatus and method based on a pyrolysis-mass spectrometry technology.

BACKGROUND

Plastic is the most common organic synthetic polymer material in daily life, which is widely applied due to its advantages such as low price, light weight and convenience in use. Statistically, in 2013, the global consumption of plastic products amounted to 300 million tons. In 2016, Greenpeace reported that about 200 kg of plastics entered the ocean in a second. Moreover, the consumption of the plastics is still increasing. Among them, about 10% of plastic wastes will enter the ocean. The remaining plastic wastes will pollute a terrestrial environment by means of approaches such as recycling, incinerating, backfilling and discarding. As the plastic wastes accumulate in the environment, they will exist for more than hundreds of years because their chemical properties are relatively stable and most of them are difficult to degrade. Massive plastics will be continuously broken into tiny plastic debris due to synergistic effects of physical, chemical and biological effects such as stormy waves, ocean currents, sunlight and marine microorganisms. In addition, facial cleansers for daily use, some cosmetics, and industrial abrasives all contain plastic particles. These plastic debris and particles are capable of continuously migrating in the environment along with rivers, wind, and ocean currents, showing a global distribution.

At present, plastic debris with a particle size of less than 5 mm are collectively referred to as microplastics. Also, some researchers believe that plastics with a particle size of less than 500 nm should be made into nanoplastics. Marine wastes of plastic were firstly reported in the 1970s. At present, the pollution caused by the plastic waste has been found in the Atlantic, Pacific, polar regions, deep seas and even plateau lakes. In 2004, British scientists published a paper on plastic debris in marine water and sediment in Science, which had attracted the worldwide attention. Moreover, more and more researchers have carried out related researches on microplastics.

Microplastics, also known as "PM2.5 in the ocean", are listed as the second largest scientific issue in the field of environmental and ecological science research, and have become a major global environmental issue alongside global climate change, ozone depletion and ocean acidification. microplastics in the ocean will seriously damage the marine environment and ecology. microplastics suspended in seawater will influence the photosynthesis of marine algae. microplastics are easily eaten by some marine organisms and are difficult to digest in the gastrointestinal tracts of the marine organisms, causing malnutrition and even death of the marine organisms. Studies have found that the microplastics may affect the spawning amount and the reproductive capacity of some marine organisms such as fish. In addition, the microplastics contain some toxic plastic additives, and have a toxic effect on surrounding organisms because organic pollutants, heavy metals are easily enriched on their surfaces. The microplastics enter the human body through the food chain and will have a non-negligible impact on the human health. In recent years, microplastic pollution has received more and more attentions. Moreover, microplastics have been detected in more and more environmental media. Meanwhile, numerous scientific studies have shown that the microplastics can be ingested by organisms of different nutritional levels and retained in the organisms for different periods of time. When these microplastics are ingested by the organisms, there are many health risks. Studies have shown that mussels may suffer from the oxidative stress therein and have a decrease in reproductive capacity when ingesting the microplastics; zebrafishes may suffer from liver metabolism disturbance when ingesting the microplastics; and crucians may suffer from the nerve injury when ingesting the microplastics. However, the microplastics do not exist alone in the environment. Some organic pollutants in the environment will interact with the microplastics. However, research on the health risks of the interaction between the microplastics and the environmental pollutants is in its initial stage.

At present, the damage to the marine ecological environment by microplastics pollution and its threat to the human health have received much serious considerations. Various researches on the microplastics are actively underway. the microplastic detection technology is a basis to support the research on the microplastics. For emerging pollutants, the microplastic detection and analysis technology is immature. The lack of methods capable of performing rapid and simultaneous qualitative and quantitative analysis is one of the important subjects of the research on the microplastics. At present, the qualitative detection for the microplastics mainly relies on three methods: Raman spectroscopy, Fourier-infrared spectroscopy and pyrolysis-gas mass spectrometry. The spectroscopic method generally has a requirement that the size is greater than 10 μm due to a size limit of a target, and easily interfered by the environment. At present, the quantitative analysis method mainly relies on microscopes and other tools to perform manual counting, which has large errors and low accuracy, and is laborious and time-consuming. The patent application with a Chinese patent application No. 201610045344.3 which was filed on Jun. 15, 2016 discloses a method for quantitatively analyzing enrichment and distribution of microplastics in mammals. The method is to quantitatively analyze enrichment and distribution of the microplastics in mammals based on a fluorescent labeling technology, which belongs to the field of environmental health risk assessment. Steps of such a method are tedious and complicated, and are interfered by many factors. Such a method has large errors and low accuracy of detection data results, and is laborious and time-consuming.

Moreover, at present, the health risk research on combined effects of the microplastics and the environmental pollutants is mostly focused on the terminal toxicity assessment, and rarely evaluates the content of organic pollutants adsorbed on the microplastics. This is because, until now, the cognition on the damages caused by the microplastics is confined to their own toxicity, there is a lack of systematic quantitative analysis of the content of the microplastics and their adsorbed pollutants into the organisms, and it is impossible to know the enrichment and distribution rule of the microplastics in main organs of the mammals, which brings many uncertainties to the toxicity assessment of the combined effects of the microplastics and the pollutants in the later period. In addition, an existing quantitative detection instrument is bulky and expensive, is high in power consumption, and may only be operated in a laboratory. The existing quantitative detection instrument is difficult to apply in shipborne, vehicle-mounted and on-site detection, which limits the investigation and research on the microplastics. Therefore, it is particularly important to establish an easy-to-operate, rapid and accurate method for qualitatively and quantitatively analyzing the microplastics and their adsorbed environmental pollutants.

SUMMARY

In order to overcome the above-mentioned shortcomings of the prior art, an objective of the present invention is to provide a microplastic detection device and method based on a pyrolysis-mass spectrometry technology, which has simple structure, low manufacturing cost, convenient operation, small environmental disturbance, small instrument volume, low power, and capable of performing on-site real-time detection, realizing rapid and accurate qualitative and quantitative analysis of multiple components of single microplastic sample, and may be applied to shipborne, vehicle-mounted and on-site detection.

The present invention solves the above technical problems and adopts the following solutions.

A microplastic detection device based on a pyrolysis-mass spectrometry technology is substantially a sealed gas path device system connected via pipelines. The device includes a working gas source, a pyrolysis device, a filter and a mass spectrometer which are connected in sequence. After a microplastic sample is placed into the pyrolysis device, the microplastic sample is decomposed in the pyrolysis device, and pyrolysis products from the microplastic sample driven by a carrier gas of the working gas source enter the mass spectrometer for detection and analysis after being filtered by the filter.

Preferably, a heating main body of the pyrolysis device is a quartz tube wrapped with an electric heating wire on its outer tube wall, two ends of the electric heating wire are respectively connected with a temperature programming device, and a temperature sensing device is connected within the quartz tube.

Preferably, the temperature sensing device is a temperature measurement wire. The temperature programming device includes a temperature measurement wire, a temperature conversion circuit, an acquisition card, a control system, a power supply and a heating module circuit which are electrically connected in sequence. After the power supply is turned on, a temperature collected by the temperature measurement wire is converted into an electrical signal by means of the temperature conversion circuit, and then the electrical signal is received by the acquisition card. An output power of the heating module circuit is adjusted by means of a PID algorithm of the control system, that is, a heating power of the electric heating wire is adjusted, and thus a heating rate within the quartz tube is adjusted.

Preferably, the quartz tube is filled with high-purity quartz fiber, and an outer surface of the electric heating wire is wrapped with high temperature-resistant thermal insulation cotton.

Preferably, the filter is a high-purity quartz fiber filter, and the high-purity quartz fiber filter is made of a quartz tube filled with high-purity quartz fiber.

Preferably, the mass spectrometer is a portable or bench mass spectrometer. The mass spectrometer is one selected from a group consisting of an ion trap mass spectrometer, a quadrupole mass spectrometer, a triple quadrupole mass spectrometer, a time-of-flight mass spectrometer, a quadrupole-time-of-flight mass spectrometer, an ion trap-time-of-flight mass spectrometer, a magnetic mass spectrometer et al.

Preferably, the working gas source is any one selected from a group consisting of argon, nitrogen and an inert gas. A flow regulating device is provided which connected to the working gas source.

A microplastic detection method based on a pyrolysis-mass spectrometry technology, using the above microplastic detection device based on a pyrolysis-mass spectrometry technology, includes the following steps:

1) adding a microplastic sample to a quartz slide within a quartz tube of a pyrolysis device, filling the quartz tube with high-purity quartz fiber, connecting a temperature measurement wire to the slide on which the sample is located within the quartz tube, and then connecting a working gas source, a pyrolysis device, a filter and a mass spectrometer in a sealing manner via pipelines;

2) turning on the working gas source to enable a carrier gas to pass from an outlet of the working gas source through the pyrolysis device and the filter to reach a sample inlet of the mass spectrometer, firstly introducing the carrier gas, and after air in the pipelines is removed, continuously introducing the carrier gas;

3) after turning on the power supply of the temperature programming device, setting a temperature-programmed process by the control system, wherein a temperature collected by the temperature measurement wire is converted into an electrical signal by means of a temperature conversion circuit, and then the electrical signal is received by the acquisition card, and then an output power of the heating module circuit is adjusted by means of a PID algorithm of the control system, that is, the temperature of an electric heating wire is adjusted, and thus a heating rate within the quartz tube is adjusted;

4) decomposing the microplastic sample in the quartz tube, and finally, transporting pyrolysis products from the microplastic sample to the mass spectrometer for detection and analysis after being filtered by the filter under drive of the carrier gas of the working gas source, thereby realizing qualitative and quantitative analysis of the microplastic sample by the mass spectrometer.

Preferably, in the step 2), the time period of introducing the carrier gas is 2 minutes or more, and after air in the pipelines is removed, continuously introducing the carrier gas.

Preferably, in the step 3), the temperature-programmed process includes the following steps: setting a heating target temperature within the quartz tube, starting a heating control program, reading a current temperature by the program, calculating a temperature difference by means of a PID algorithm, and adjusting an output power of the heating module to achieve full power output and rapid temperature increase; and wherein when a current temperature is close to the set target temperature and a temperature difference is decreased, reducing the power output; when the current temperature is greater than the set target temperature, stopping heating; and when the current temperature is lower than the set target temperature, starting heating, and adjusting the output power and keeping the temperature stable according to the temperature difference.

The present invention has the following beneficial effects.

(1) The present invention provides a microplastic detection device and method based on a pyrolysis-mass spectrometry technology. The microplastic detection device has simple structure, convenient operation, without additional external heating devices and gas phase separation devices in the entire gas path transmission process, low manufacturing cost, small environmental interference, small instrument volume, low power, and portable design, and enable rapid on-site detection and laboratory detection and analysis. The microplastic detection device achieves a portable design in combination with a portable mass spectrometric detection device, and may be applied to shipborne, vehicle-mounted and on-site detection.

(2) The present invention provides a microplastic detection device and method based on a pyrolysis-mass spectrometry technology. The microplastic detection device is based on the pyrolysis-mass spectrometry technology, which is capable of simply and effectively performing qualitative and quantitative analysis on the microplastics and components of their adsorbed pollutants, so as provide reliable basic data for the health risk assessment of combined effects of the microplastics and the pollutants in the later period.

(3) The present invention provides a microplastic detection method based on a pyrolysis-mass spectrometry technology. The microplastic detection method is easy and rapid to operate, and is capable of simultaneously performing qualitative and quantitative analysis on multiple kinds of microplastic samples. A gradual heating manner may be selected to separately detect a variety of different plastic components in the microplastics. Accordingly, the detection accuracy is significantly improved. Further, a rapid heating method may be employed to rapidly and simultaneously detect multiple kinds of plastics.

BRIEF DESCRIPTION OF THE DRAWINGS

FIG. 1 is a schematic diagram showing the structure of the present invention.

Reference numerals in the drawing: 1. working gas source; 2. pyrolysis device; 3. filter; 4. mass spectrometer; 5. temperature programming device; and 6. temperature sensing device.

DESCRIPTION OF THE EMBODIMENTS

The present invention will be further described below in conjunction with accompanying drawings and specific embodiments to help understand the present invention. Methods used in the present invention are conventional production methods unless otherwise stated. Raw materials and apparatuses used are conventional commercial products unless otherwise stated.

A First Embodiment

As shown in FIG. 1, a microplastic detection device based on a pyrolysis-mass spectrometry technology is a sealed gas path device system formed by connection via pipelines as a whole. The device includes a working gas source 1, a pyrolysis device 2, a filter 3, and a mass spectrometer 4 which are connected in sequence. After a microplastic sample is put into the pyrolysis device 2, the microplastic sample is decomposed in the pyrolysis device 2, and pyrolysis products from the microplastic sample enter the mass spectrometer 4 for detection and analysis after being filtered by the filter 3 under the drive of a carrier gas of a working gas source 1. By means of species and peak areas of the pyrolysis products, rapid qualitative and quantitative analysis of microplastic sample is performed. The microplastic detection device has simple structure and convenient operation, may realize accurate qualitative and quantitative analysis on the microplastics and their absorbed pollutants, and provides reliable basic data to health risk evaluation on combined effects of the microplastics and the pollutants in the later period.

A heating main body of the pyrolysis device 2 is a quartz tube wrapped with an electric heating wire on its outer wall. Two ends of the electric heating wire are respectively connected with a temperature programming device 5, and the electric heating wire is tightly sleeved on the quartz tube, and an outer surface of the electric heating wire is covered with high-temperature-resistant thermal insulation cotton for thermal insulation. A temperature sensing device 6 is disposed within the quartz tube in a connecting manner, the microplastic sample is placed on a slide within the quartz tube, and a temperature measurement head is connected with the slide to ensure accurate measurement of a plastic pyrolysis temperature. Moreover, the quartz tube is filled with high-purity quartz fiber for fixing the slide on which the sample is located to absorb impurities. The high-purity quartz fiber is filled in a pyrolysis device 2, which may effectively improve the heating efficiency, and prevent the impurities such as pyrolysis ashes generated during the pyrolysis of the microplastic sample from entering the mass spectrometer 4.

The filter 3 is a high-purity quartz fiber filter. The high-purity quartz fiber filter is made of a quartz tube filled with high-purity quartz fiber. After the filter 3 is mounted on the pyrolysis device 2, ashes that may be generated after the microplastic sample is decomposed, impurities and other solid impurities may be further filtered, and the decomposed impurities and possible condensation products are further filtered. Accordingly, it is possible to ensure that purely cracked gas products enter the mass spectrometer 4.

The temperature sensing device 6 is a high-temperature-resistant temperature measurement wire. The temperature measurement wire is a K-type thermocouple temperature measurement wire. The temperature programming device 5 includes a temperature measurement wire, a temperature conversion circuit, an acquisition card, a control system, a power supply and a heating module circuit which are electrically connected in sequence. After the power supply is turned on, a temperature collected by the temperature measurement wire is converted into an electrical signal by means of a temperature conversion circuit, and then the electrical signal is received by the acquisition card. A target temperature within the quartz tube is set. An output power of the heating module is adjusted by means of a PID algorithm of the control system, and further a heating rate within the quartz tube is adjusted. Accordingly, it is possible to ensure rapid temperature increase and maintain temperature stability. A temperature difference is calculated by means of a PID algorithm, when the temperature difference is relatively high, an output power of the heating module is adjusted to achieve full power output and rapid temperature increase; and when a current temperature is close to the set target temperature, the temperature difference is decreased and the power output is reduced; when the current temperature is greater than the set target temperature, the heating is stopped, and when the current temperature is lower than the set target temperature, the heating is started, and the output power is adjusted and the temperature is kept stably at the target temperature according to the temperature difference.

The mass spectrometer 4 is a portable or desk type mass spectrometer, preferably a portable quadrupole mass spectrometer, which has a mass detection device with a gas detection capability, low power consumption, low price, and is portable due to miniaturization, and may be applied shipborne, vehicle-mounted and on-site detection, thereby facilitating real-time on-site investigation and detection of the microplastics in the environment.

The working gas source 1 is argon so that the gas pipelines of the device maintain good airtightness to isolate external gas interference. A flow adjustment device is connected to the working gas source 1, which facilitates the adjustment of the flow and the flow rate of the carrier gas in the gas path in the entire device according to samples in different conditions.

A microplastic detection method based on a pyrolysis-mass spectrometry technology, using the microplastic detection device based on the above pyrolysis-mass spectrometry technology, includes the following steps:

1) adding a microplastic sample to a quartz slide within a quartz tube of a pyrolysis device 2, filling the quartz tube with high-purity quartz fiber, connecting a temperature measurement wire to the slide on which the sample is located within the quartz tube to ensure accurate measurement of a plastic pyrolysis temperature, and then connecting a working gas source 1, a pyrolysis device 2, a filter 3 and a mass spectrometer 4 in a sealing manner via pipelines;

2) turning on the working gas source to enable a carrier gas of the working gas source to sequentially pass through the pyrolysis device 2 and the filter 3 to a sample inlet of the mass spectrometer 4, firstly introducing the carrier gas for 2 min, and after air in the pipelines is removed, continuously introducing the carrier gas;

3) after the power supply of the temperature programming device 5 is turned on, setting a temperature-programmed process by the control system, wherein the temperature-programmed process includes the following steps: setting a heating target temperature within the quartz tube, starting a heating control program, reading a current temperature by the program, calculating a temperature difference by means of a PID algorithm, when the temperature difference is relatively large, regulating an output power of the heating module to achieve full power output and rapid temperature increase; and when the current temperature is close to the set target temperature, decreasing the temperature difference and reducing the power output; when the current temperature is greater than the set target temperature, stopping heating; and when the current temperature is lower than the set target temperature, starting heating, and adjusting the output power and keeping the temperature stably at the target temperature according to the temperature difference, wherein a temperature collected by the temperature measurement wire is converted into an electrical signal by means of a temperature conversion circuit, and then the electrical signal is received by the acquisition card, and then an output power of the heating module circuit is adjusted by means of a PID algorithm of the control system, that is, a heating power of an electric heating wire is adjusted, and further a heating rate within the quartz tube is adjusted; and 4) the microplastic sample is decomposed in the quartz tube, and pyrolysis products from the microplastic sample are transported to the mass spectrometer 4 for detection and analysis after being filtered by the filter 3 under the drive of the carrier gas of the working gas source 1, so that qualitative and quantitative analysis of microplastic sample is performed by the mass spectrometer 4.

After the pyrolysis products enter the mass spectrometer 4, a mass spectrum is obtained. The species of plastics may be effectively determined by determining characteristic peaks of the products and an intensity ratio of the characteristic peaks. For example, mass-to-charge ratios of characteristic peaks of pyrolysis products of polyethylene include 83, 85, 97, and so on, and mass-to-charge ratios of characteristic peaks of pyrolysis products of polypropylene include 69, and so on. In addition, the quality of the sample may be further derived by calculating the peak area of the characteristic peaks in combination with a linear relationship between the products and the quality of the raw materials.

Since there are many species of microplastics in the environment and there are differences in pyrolysis temperatures of multiple plastics, by increasing the temperature to pyrolysis temperatures of different samples by means of the temperature programming device 5 and remaining it stable, different plastics may be separately detected and the detection accuracy may be improved. Furthermore, the temperature may be rapidly increased to a higher temperature, so that multiple samples are simultaneously detected. Therefore, the detection time is shortened.

In summary, compared with the traditional pyrolysis-gas mass spectrometer, the present invention adopts the pyrolysis device 2 with the temperature programming device 5. A gradual heating manner may be employed to separately detect various plastic components in the microplastics and improve the detection accuracy. Further, a rapid heating manner may be employed to rapidly and simultaneously detect a variety of plastics. In the entire process of transporting the carrier gas along the gas path, no additional external heating device and gas phase separation device are needed. Therefore, the present invention is convenient to operate, low in manufacturing cost, and portable in design due to combination with a portable mass spectrometry device, and may be applied to shipborne, vehicle-mounted and son-site detection. The detection method based on the device is simple and rapid, and enable qualitative and quantitative analysis of multiple microplastic samples.

What stated above are merely preferred embodiments of the present invention, but are not intended to limit implementation ranges of the present invention. For example, the mass spectrometer 4 is one of a portable or desk type ion trap mass spectrometer, a quadrupole mass spectrometer, a triple quadrupole mass spectrometer, a time-of-flight mass spectrometer, a quadrupole-time-of-flight mass spectrometer, an ion trap-time-of-flight mass spectrometer and a magnetic mass spectrometer. The working gas source 1 is any one of argon, nitrogen or an inert gas. The microplastic detection device and method based on the pyrolysis-mass spectrometry technology of the present invention may be realized.

In the description of the present invention, it should be understood that orientational or positional relationships indicated by terms "upper", "lower", "inner", "outer", "bottom" and "center" are based on orientational or positional relationships shown in the drawing, which is only for the convenience of describing the present invention and simplifying the description, rather than indicating or implying that the described device or element must have a specific orientation and is constructed and operated in a specific orientation, and therefore should not be construed as a limitation of the present invention.

However, what stated above are merely preferred embodiments of the present invention, but are not intended to limit implementation ranges of the present invention. All equivalent changes and modifications made in accordance with the scope of the present invention shall fall within the scope of the present invention.

What is claimed is:

1. A microplastic detection device based on a pyrolysis-mass spectrometry technology, wherein the microplastic detection device is substantially a sealed gas path device system connected via pipelines, the microplastic detection device comprises a working gas source, a pyrolysis device, a filter and a mass spectrometer connected in sequence, wherein a microplastic sample is placed into the pyrolysis device, the microplastic sample is decomposed in the pyrolysis device, and pyrolysis products from the microplastic sample driven by a carrier gas of the working gas source enter the mass spectrometer for detection and analysis after being filtered by the filter.

2. The microplastic detection device based on a pyrolysis-mass spectrometry technology according to claim 1, wherein a heating main body of the pyrolysis device is a quartz tube wrapped with an electric heating wire on its outer tube wall, two ends of the electric heating wire are respectively connected with a temperature programming device, and a temperature sensing device is connected within the quartz tube.

3. The microplastic detection device based on a pyrolysis-mass spectrometry technology according to claim 2, wherein the temperature sensing device is a temperature measurement wire; and the temperature programming device comprises a temperature measurement wire, a temperature conversion circuit, an acquisition card, a control system, a power supply and a heating module circuit which are electrically connected in sequence, wherein after the power supply is turned on, a temperature collected by the temperature measurement wire is converted into an electrical signal by means of the temperature conversion circuit, and then the electrical signal is received by the acquisition card; and an output power of the heating module circuit is adjusted by means of a PID algorithm of the control system, that is, a heating power of an electric heating wire connected with the heating module circuit is adjusted, and thus a heating rate within the quartz tube is adjusted.

4. The microplastic detection device based on a pyrolysis-mass spectrometry technology according to claim 2, wherein the quartz tube is filled with high-purity quartz fiber, and an outer surface of the electric heating wire is wrapped with high-temperature-resistant thermal insulation cotton.

5. The microplastic detection device based on a pyrolysis-mass spectrometry technology according to claim 1, wherein the filter is a high-purity quartz fiber filter, and the high-purity quartz fiber filter is made of a quartz tube filled with high-purity quartz fiber.

6. The microplastic detection device based on a pyrolysis-mass spectrometry technology according to claim 1, wherein the mass spectrometer is a portable or bench mass spectrometer, and the mass spectrometer is one selected from a group consisting of an ion trap mass spectrometer, a quadrupole mass spectrometer, a triple quadrupole mass spectrometer, a time-of-flight mass spectrometer, a quadrupole-time-of-flight mass spectrometer, an ion trap-time-of-flight mass spectrometer and a magnetic mass spectrometer.

7. The microplastic detection device based on a pyrolysis-mass spectrometry technology according to claim 1, wherein the working gas source is any one selected from a group consisting of argon, nitrogen and an inert gas, and a flow regulating device is provided which is connected to the working gas source.

8. A microplastic detection method based on a pyrolysis-mass spectrometry technology by using the microplastic detection device based on pyrolysis-mass spectrometry technology according to claim 1, the microplastic detection method comprising the following steps:
1) adding a microplastic sample to a quartz slide within a quartz tube of a pyrolysis device, filling the quartz tube with high-purity quartz fiber, connecting a temperature measurement wire onto the slide on which the sample is located within the quartz tube, and then connecting a working gas source, a pyrolysis device, a filter and a mass spectrometer in a sealing manner via pipelines;
2) turning on the working gas source and regulating a gas flow to enable a working gas to sequentially pass through the flow regulating device, the pyrolysis device and the filter to reach a sample inlet of the mass spectrometer, firstly introducing the carrier gas, and after air in the pipelines is removed, continuously introducing the carrier gas;
3) after turning on the power supply of the temperature programming device, setting a temperature-programmed process by the control system, wherein a temperature collected by the temperature measurement wire is converted into an electrical signal by means of a temperature conversion circuit, and then the electrical signal is received by the acquisition card, and then an output power of the heating module circuit is adjusted by means of a PID algorithm of the control system, that is, a heating power of an electric heating wire is adjusted, and thus a heating rate within the quartz tube is adjusted; and
4) decomposing the microplastic sample in the quartz tube, and transporting pyrolysis products from the microplastic sample to the mass spectrometer for detection and analysis after being filtered by the filter under drive of the carrier gas of the working gas source, so that qualitative and quantitative analysis of the microplastic sample is realized by the mass spectrometer.

9. The microplastic detection method based on a pyrolysis-mass spectrometry technology according to claim 8, wherein in the step 2), the time period of introducing the carrier gas is 2 minutes or more, and air within the pipelines is removed.

10. The microplastic detection method based on a pyrolysis-mass spectrometry technology according to claim 8, wherein in the step 3), the temperature-programmed process comprises the following steps: setting a heating target temperature within the quartz tube, starting a heating control program, reading a current temperature by the program, calculating a temperature difference by means of a PID algorithm, adjusting an output power of the heating module to achieve full power output and rapid temperature increase; and wherein when a current temperature is close to the set target temperature and a temperature difference is decreased, reducing the power output; when the current temperature is greater than the set target temperature, stopping heating; and when the current temperature is lower than the set target temperature, starting heating, and adjusting the output power according to the temperature difference.

* * * * *